(12) United States Patent
Gaines et al.

(10) Patent No.: US 7,998,109 B2
(45) Date of Patent: Aug. 16, 2011

(54) RE-CERTIFICATION SYSTEM FOR A FLOW CONTROL APPARATUS

(75) Inventors: Robert B. Gaines, Lake Saint Louis, MO (US); Christopher A. Knauper, Lake St. Louis, MO (US); Jeffrey E. Price, Wildwood, MO (US)

(73) Assignee: Covidien AG (CH)

( * ) Notice: Subject to any disclaimer, the term of this patent is extended or adjusted under 35 U.S.C. 154(b) by 140 days.

(21) Appl. No.: 12/496,842

(22) Filed: Jul. 2, 2009

(65) Prior Publication Data

US 2010/0030361 A1 Feb. 4, 2010

Related U.S. Application Data

(63) Continuation of application No. 10/854,008, filed on May 25, 2004, now Pat. No. 7,794,423.

(51) Int. Cl.
*A61M 31/00* (2006.01)
(52) U.S. Cl. ........................................... 604/65
(58) Field of Classification Search .............. 604/65–67, 604/30, 31, 32, 33, 34, 6.1, 9, 99.02, 99.03, 604/99.04, 167.03, 236, 237, 247, 251, 253; 128/DIG. 12, DIG. 13
See application file for complete search history.

(56) References Cited

U.S. PATENT DOCUMENTS

| | | | |
|---|---|---|---|
| 3,626,938 A | 12/1971 | Versaci | |
| 3,896,803 A | 7/1975 | Mason | |
| 3,985,133 A | 10/1976 | Jenkins et al. | |
| 4,396,385 A | 8/1983 | Kelly et al. | |
| 4,460,355 A | 7/1984 | Layman | |
| 4,460,366 A | 7/1984 | Shinno | |
| 4,519,792 A | 5/1985 | Dawe | |
| 4,557,725 A | 12/1985 | Heyne et al. | |
| 4,604,093 A | 8/1986 | Brown et al. | |
| 4,605,396 A | 8/1986 | Tseo et al. | |
| 4,685,910 A | 8/1987 | Schweizer | |
| D293,129 S | 12/1987 | Millerd et al. | |
| 4,710,166 A | 12/1987 | Thompson et al. | |
| 4,714,463 A | 12/1987 | Archibald et al. | |
| 4,741,736 A | 5/1988 | Brown | |
| 4,789,000 A | 12/1988 | Aslanian | |
| 4,798,590 A | 1/1989 | O'Leary et al. | |
| 4,820,268 A | 4/1989 | Kawamura et al. | |
| 4,831,866 A | 5/1989 | Forkert et al. | |

(Continued)

FOREIGN PATENT DOCUMENTS

DE 4020522 A1 1/1992

(Continued)

OTHER PUBLICATIONS

Response filed Jan. 26, 2010 to Office Action dated Sep. 4, 2009 from related U.S. Appl. No. 10/854,008; 9 pgs.

(Continued)

*Primary Examiner* — Manuel A Mendez

(57) ABSTRACT

A flow control apparatus includes a flow control apparatus adapted to load a re-certification feeding set. The apparatus further includes a software subsystem in communication with the flow control apparatus having a re-certification procedure that determines whether a user has performed manual tests on the apparatus to verify that at least one component of the apparatus is functioning within a predetermined operational range. The subsystem disables automatic testing if it determines that manual testing has not been performed and executes a reiterative process prompting the user to conduct manual testing if the subsystem determines that manual testing has been performed.

13 Claims, 15 Drawing Sheets

U.S. PATENT DOCUMENTS

| | | | |
|---|---|---|---|
| 4,838,856 A | 6/1989 | Mulreany et al. | |
| 4,840,542 A | 6/1989 | Abbott | |
| 4,845,487 A | 7/1989 | Frantz et al. | |
| 4,850,805 A | 7/1989 | Madsen et al. | |
| 4,850,980 A | 7/1989 | Lentz et al. | |
| 4,884,103 A | 11/1989 | Yamada | |
| 4,898,581 A | 2/1990 | Iwatschenko | |
| 4,913,703 A | 4/1990 | Pasqualucci et al. | |
| 4,915,688 A | 4/1990 | Bischof et al. | |
| 4,918,973 A | 4/1990 | Kruse | |
| 4,919,596 A | 4/1990 | Slate et al. | |
| 4,950,254 A | 8/1990 | Andersen et al. | |
| 4,955,860 A | 9/1990 | Ruano | |
| 5,057,081 A | 10/1991 | Sunderland et al. | |
| 5,084,031 A | 1/1992 | Todd et al. | |
| 5,111,683 A | 5/1992 | Fond | |
| 5,147,313 A | 9/1992 | Dikeman | |
| 5,158,437 A | 10/1992 | Natwick et al. | |
| 5,171,029 A | 12/1992 | Maxwell et al. | |
| 5,181,910 A | 1/1993 | Scanlon | |
| 5,197,322 A | 3/1993 | Indravudh | |
| 5,201,711 A | 4/1993 | Pasqualucci et al. | |
| 5,213,483 A | 5/1993 | Flaherty et al. | |
| 5,244,463 A | 9/1993 | Cordner, Jr. et al. | |
| 5,253,640 A | 10/1993 | Falb et al. | |
| 5,272,917 A | 12/1993 | Pippert | |
| 5,299,446 A | 4/1994 | Pardinas et al. | |
| 5,318,413 A | 6/1994 | Bertoncini | |
| 5,364,364 A | 11/1994 | Kasvikis et al. | |
| 5,368,562 A | 11/1994 | Blomquist et al. | |
| 5,374,248 A | 12/1994 | Lopez | |
| 5,374,251 A | 12/1994 | Smith | |
| 5,415,641 A | 5/1995 | Yerlikaya et al. | |
| 5,431,627 A | 7/1995 | Pastrone et al. | |
| 5,437,642 A | 8/1995 | Thill et al. | |
| 5,439,452 A | 8/1995 | McCarty | |
| 5,443,543 A | 8/1995 | Epes et al. | |
| 5,499,968 A | 3/1996 | Milijasevic et al. | |
| 5,531,680 A | 7/1996 | Dumas et al. | |
| 5,531,697 A | 7/1996 | Olsen et al. | |
| 5,562,615 A | 10/1996 | Nassif | |
| 5,569,026 A | 10/1996 | Novak | |
| 5,584,671 A | 12/1996 | Schweitzer, Jr. et al. | |
| 5,589,026 A | 12/1996 | Perecman | |
| 5,603,353 A | 2/1997 | Clark et al. | |
| 5,634,907 A | 6/1997 | Rani et al. | |
| 5,681,294 A | 10/1997 | Osborne et al. | |
| 5,704,584 A | 1/1998 | Winterer et al. | |
| 5,755,683 A | 5/1998 | Houle et al. | |
| 5,772,637 A | 6/1998 | Heinzmann et al. | |
| 5,807,321 A | 9/1998 | Stoker et al. | |
| 5,807,333 A | 9/1998 | Osborne et al. | |
| 5,814,015 A | 9/1998 | Gargano et al. | |
| 5,840,058 A | 11/1998 | Ammann et al. | |
| 5,951,510 A | 9/1999 | Barak | |
| 6,042,564 A | 3/2000 | Barak | |
| 6,059,544 A | 5/2000 | Jung et al. | |
| 6,117,115 A | 9/2000 | Hill et al. | |
| 6,139,748 A | 10/2000 | Ericson et al. | |
| 6,142,979 A | 11/2000 | McNally et al. | |
| 6,164,921 A | 12/2000 | Moubayed et al. | |
| 6,250,130 B1 | 6/2001 | Howard et al. | |
| 6,280,440 B1 | 8/2001 | Gocho | |
| 6,283,719 B1 | 9/2001 | Frantz et al. | |
| 6,364,857 B1 | 4/2002 | Gray et al. | |
| 6,368,314 B1 | 4/2002 | Kipfer et al. | |
| 6,422,057 B1 | 7/2002 | Anderson | |
| 6,491,659 B1 | 12/2002 | Miyamoto | |
| 6,530,907 B1 | 3/2003 | Sugahara et al. | |
| 6,582,387 B2 | 6/2003 | Derek et al. | |
| 6,626,862 B1 | 9/2003 | Duchon et al. | |
| 6,641,562 B1 | 11/2003 | Peterson | |
| 6,659,976 B2 | 12/2003 | Beck et al. | |
| 6,666,821 B2 | 12/2003 | Keimel | |
| 6,880,808 B2 | 4/2005 | McPeak et al. | |
| 6,942,636 B2 | 9/2005 | Holst et al. | |
| 6,985,870 B2 * | 1/2006 | Martucci et al. | 705/3 |
| 7,092,797 B2 | 8/2006 | Gaines et al. | |
| 7,469,716 B2 | 12/2008 | Parrino et al. | |
| 7,661,582 B2 | 2/2010 | Mollstam | |
| 7,794,423 B2 * | 9/2010 | Gaines et al. | 604/65 |
| 2001/0031944 A1 | 10/2001 | Peterson et al. | |
| 2002/0169424 A1 | 11/2002 | Miles et al. | |
| 2005/0278054 A1 | 12/2005 | Gaines et al. | |

FOREIGN PATENT DOCUMENTS

| | | |
|---|---|---|
| EP | 0398583 A2 | 11/1990 |
| JP | 11-002358 A | 1/1999 |
| NL | 9500612 A | 11/1996 |
| WO | 9407556 A1 | 4/1994 |
| WO | 9720594 A1 | 6/1997 |
| WO | 0126714 A1 | 4/2001 |
| WO | 03029706 A1 | 4/2003 |
| WO | 2004028595 A1 | 4/2004 |

OTHER PUBLICATIONS

Office action dated Jun. 3, 2010 from related U.S. Appl. No. 12/496,862; 6 pgs.

European Search Report for Application No. 05755565.8 dated Apr. 9, 2009, 3 pages.

Office action dated Jul. 22, 2008 from related U.S. Appl. No. 10/854,008, 5 pages.

Response filed Nov. 25, 2008 to Office action dated Jul. 22, 2008 in related U.S. Appl. No. 10/854,008, 8 pages.

Office action dated Sep. 4, 2009 from related U.S. Appl. No. 10/854,008, 8 pgs.

* cited by examiner

RE-CERTIFICATION SYSTEM FOR A FLOW CONTROL APPARATUS

CROSS-REFERENCE OF RELATED CASES

This is a continuation of co-pending U.S. patent application Ser. No. 10/854,008 filed May 25, 2004, the entirety of which is hereby incorporated by reference.

FIELD OF THE INVENTION

The present invention relates to a flow control apparatus adapted to load with a re-certification feeding set.

BACKGROUND OF THE INVENTION

Administering fluids containing medicine or nutrition to a patient is generally well known in the art. Typically, fluid is delivered to the patient by a re-certification feeding set loaded to a flow control apparatus, such as a pump, connected to a source of fluid which delivers fluid to a patient at a controlled rate of delivery. However, there is a need in the art for an improved flow control apparatus having a recertification procedure that verifies at least one component of the flow control apparatus is functioning within a predetermined operational range.

SUMMARY OF THE INVENTION

In one aspect of the present invention, a flow control apparatus generally comprises a flow control apparatus adapted to load a re-certification feeding set. The apparatus further comprises a software subsystem in communication with the flow control apparatus comprising a re-certification procedure that determines whether a user has performed manual tests on the apparatus to verify that at least one component of the apparatus is functioning within a predetermined operational range. The subsystem disables automatic testing if it determines that manual testing has not been performed and executes a reiterative process prompting the user to conduct manual testing if the subsystem determines that manual testing has been performed.

In another aspect of the present invention, a flow control apparatus generally comprises a flow control apparatus adapted to load a re-certification feeding set. The apparatus further comprises a sensor for sensing the loading of the re-certification feeding set to the flow control apparatus. A software subsystem is in operative association with the sensor. The software subsystem comprises a re-certification procedure to verify that at least one component of the flow control apparatus related to driving fluid through the re-certification feeding set is functioning within a predetermined operational range.

Other objects and features will be in part apparent and in part pointed out hereinafter.

BRIEF DESCRIPTION OF THE DRAWINGS

Corresponding reference characters indicate corresponding parts throughout the drawings.

DESCRIPTION OF THE PREFERRED EMBODIMENTS

Figure 1:
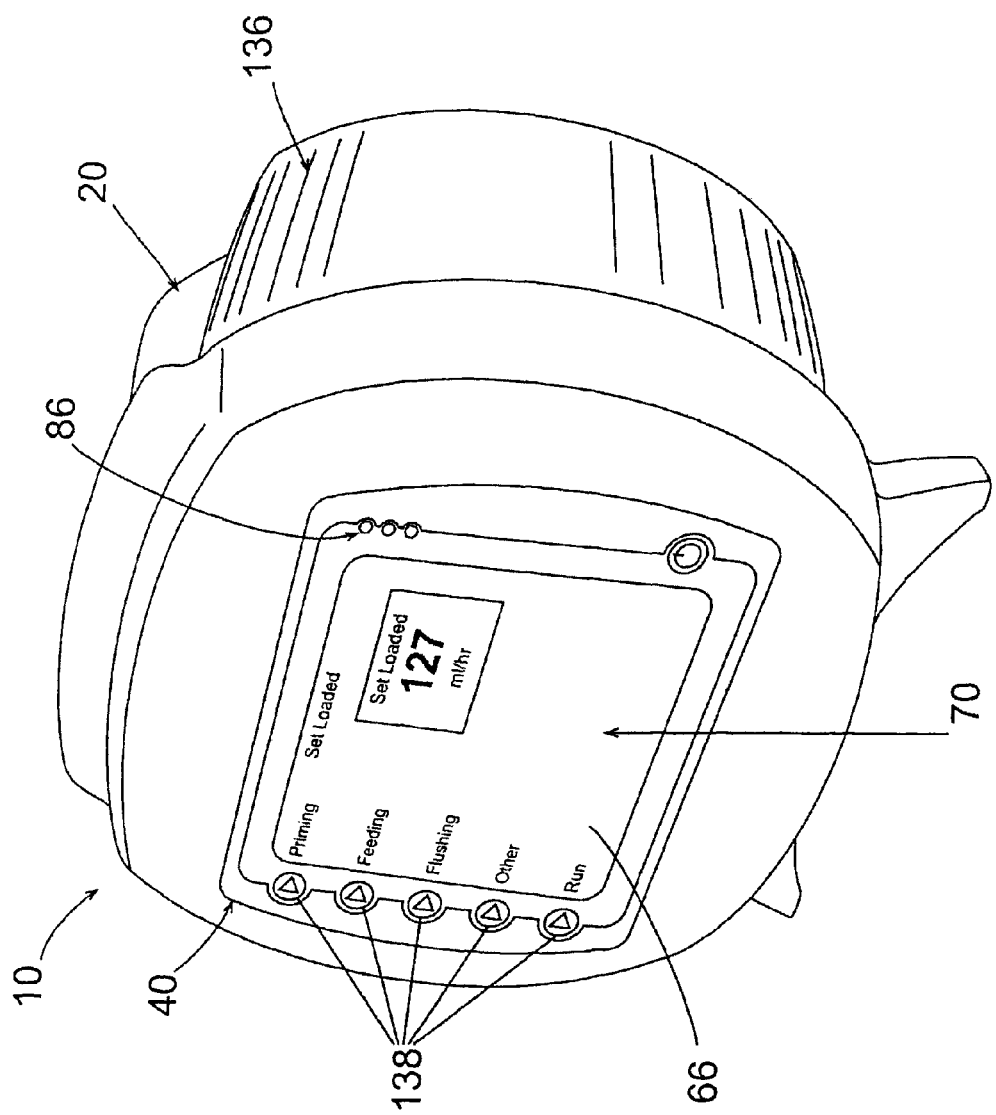
FIG. 1 is a perspective view of an exemplary flow control apparatus according to the present invention.
Figure 2:
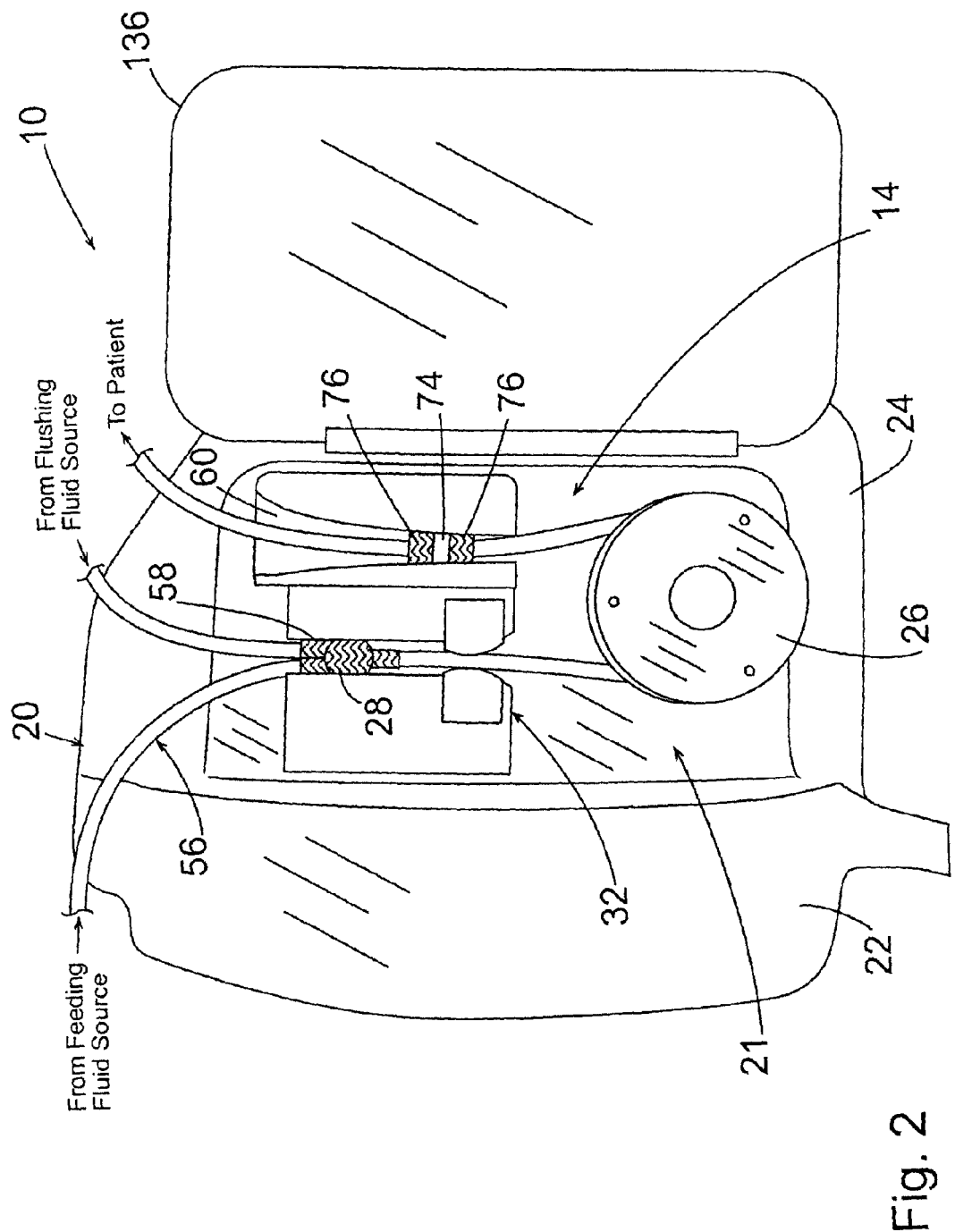
FIG. 2 is a side view of the flow control apparatus having a re-certification feeding set loaded thereto according to the present invention.
Figure 3:
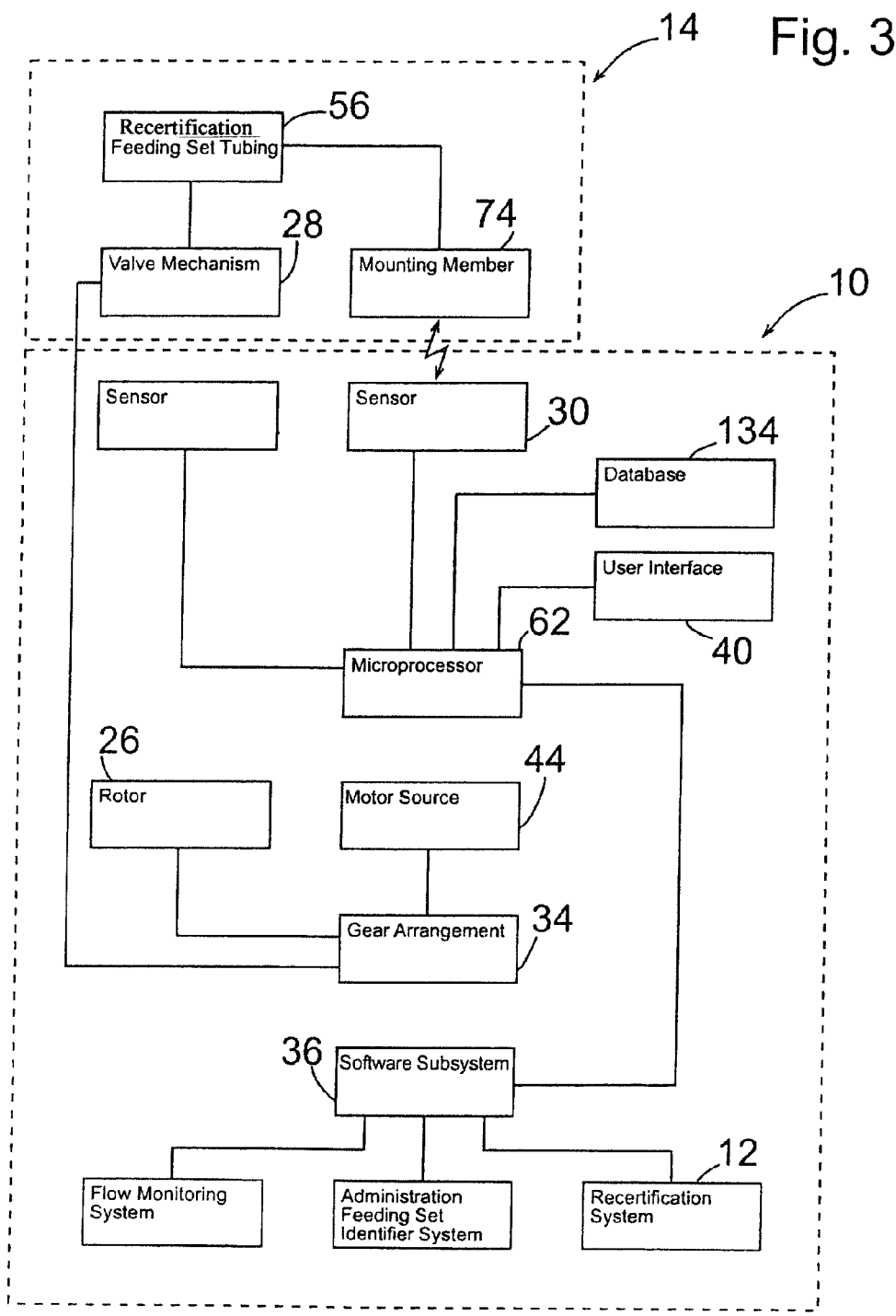
FIG. 3 is a simplified block diagram illustrating the elements of the flow control apparatus according to the present invention.

Referring to the drawings, an embodiment of the flow control apparatus according to the present invention is illustrated and generally indicated as 10 in FIGS. 1-3. Flow control apparatus 10 comprises a re-certification procedure that is capable of verifying that at least one component of the flow control apparatus 10 is functioning within a predetermined operational range when a re-certification feeding set 14 is loaded to the flow control apparatus 10. The re-certification feeding set 14 includes tubing 56 engaged to a valve mechanism 28 and mounting member 74 that load the re-certification feeding set 14 to the flow control apparatus 10 for driving fluid through the tubing 56 for delivery to a patient. As used herein the term load means that the valve mechanism 28 and mounting member 74 are engaged to the flow control apparatus 10 and tubing 56 is in a stretched condition between valve mechanism 28 and mounting member 74 such that the re-certification feeding set 14 is ready for operation with flow control apparatus 10.

Referring to FIGS. 1 and 2, an exemplary flow control apparatus 10 according to the present invention comprises a housing 20 adapted for loading the re-certification feeding set 14 to the flow control apparatus 10. Flow control apparatus 10 comprises a main recess 21 covered by a main door 136 and includes first and second recesses 58 and 60 for providing sites that are adapted to load the re-certification feeding set 14 to the flow control apparatus 10. Preferably, a means for driving fluid, such as a rotor 26, is rotatably engaged through housing 20 and adapted to engage tubing 56 such that tubing 56 is in a stretched condition between first and second recesses 58, 60 when the valve mechanism 28 and mounting member 74 are engaged to the flow control apparatus 10.

As used herein, the portion of tubing 56 of recertification feeding set 14 leading to rotor 26 is termed upstream, while the portion of tubing 56 leading away from rotor 26 is termed downstream. Accordingly, rotation of rotor 26 compresses tubing 56 and provides a means for driving fluid from the upstream to the downstream side of the re-certification feeding set 14 for delivery to a patient. The present invention contemplates that any flow control apparatus having a means for driving fluid may be used, such as a linear peristaltic pump, bellows pump, turbine pump, rotary peristaltic pump, and displacement pump Referring to FIG. 1, flow control apparatus 10 further comprises a user interface 40 that assists the user to operatively interface with the flow control apparatus 10. A display 70, in operative association with a plurality of buttons 138 positioned along an overlay 66, provide the user a means to interact with a microprocessor 62 to operate the re-certification procedure of the present invention.

According to another aspect of the present invention, a software subsystem 36 operates the re-certification procedure that is capable of verifying that at least one component of flow control apparatus 10 is functioning within a predetermined operational range once a re-certification feeding set 14 (FIG. 3) is loaded thereto.

The re-certification feeding set 14 comprises a mounting member 74 having one or more identification members 76 attached thereto that designate the re-certification feeding set 14 as having a re-certification configuration to microprocessor 62 when sensed by flow control apparatus 10. Once the user loads the re-certification feeding set 14 to flow control apparatus 10, the sensor 30 senses the presence of the mounting member 74 engaged to the second recess 60 due to the location of one or more identification members 76 attached to the mounting member 74 and signals software subsystem 36 to initiate the recertification procedure that verifies that at least one component of the flow control apparatus 10 is functioning within a predetermined operational range. Preferably identification members 76 are magnetic components, or in the alternative, magnetically-susceptible metallic components capable of being sensed by sensor 30 without requiring direct physical contact with sensor 30. Sensor 30 is preferably a Hall-effect sensor or other type of proximity sensor that is positioned near the second recess 60 such that sensor 30 can sense the presence of one or more identification members 76 when the mounting member 74 is engaged to second recess 60.

Referring to FIG. 3 software subsystem 36 directs flow 20 control apparatus 10 to perform various manual and automatic tests related to verifying that at least one component of the flow control apparatus 10 is functioning within a predetermined operational range. For example, components of the flow control apparatus 10 that may be tested during the re-certification 25 procedure can be the user interface 40, LED lights 86, sensor 30, rotor 26, valve mechanism 28, single motor source 44 and gear arrangement 34. In operation, the user loads a recertification feeding set 14 to the flow control apparatus 10 in the manner as described above and illustrated in FIG. 2 in order to initiate the re-certification procedure.

Once the mounting member 74 is engaged to the second recess 60 and the presence of the mounting member 74 is sensed by the sensor 30, the software subsystem 36 initiates the recertification procedure that instructs the microprocessor 62 to verify that at least one component of flow control apparatus 10 is functioning within a predetermined operational range.

As shown in FIGS. 5A-I the user will be instructed to follow a sequence of screens displayed on user interface 40 that controls the re-certification procedure. In addition, the software subsystem 36 performs a manual test for verifying that certain components are functioning properly and an automatic test that operates rotor 26 in order to drive a predetermined volume of fluid through the re-certification feeding set 14 to evaluate the performance of components of the flow control apparatus 10 that relate to the function of driving fluid through feeding set 14 by flow control apparatus 10. After these tests have been successfully performed, the user interface 40 is provided with a determination whether the components tested by the flow control apparatus 10 are functioning within a predetermined operational range.

Software subsystem 36 in operative association with microprocessor 62 determines through a series of decision points and steps whether at least one component of the flow control apparatus 10 is functioning within a predetermined operational range.

Figure 4:
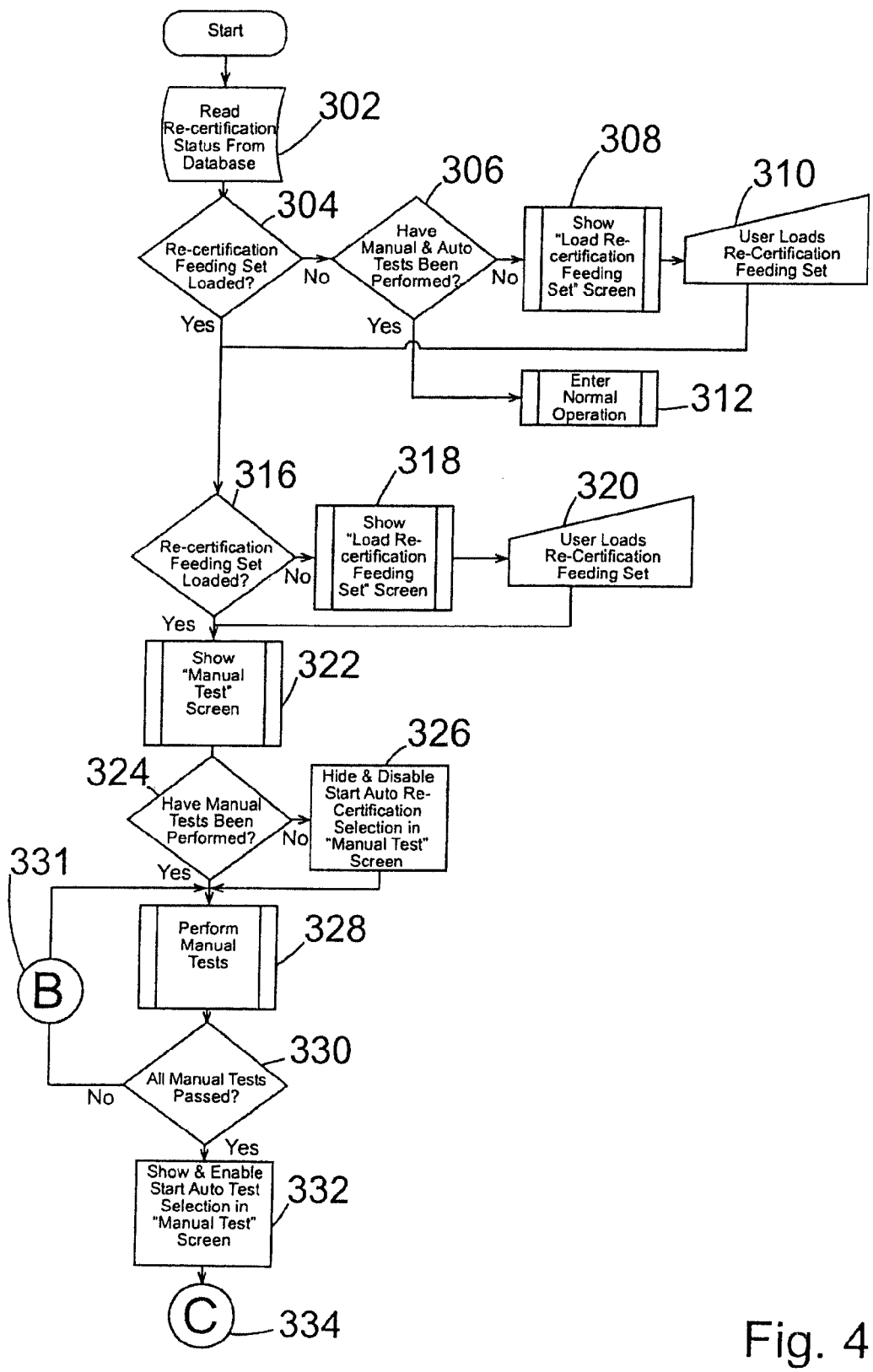
FIG. 4 is a flow chart of a re-certification procedure according to the present invention.
Figure 4A:
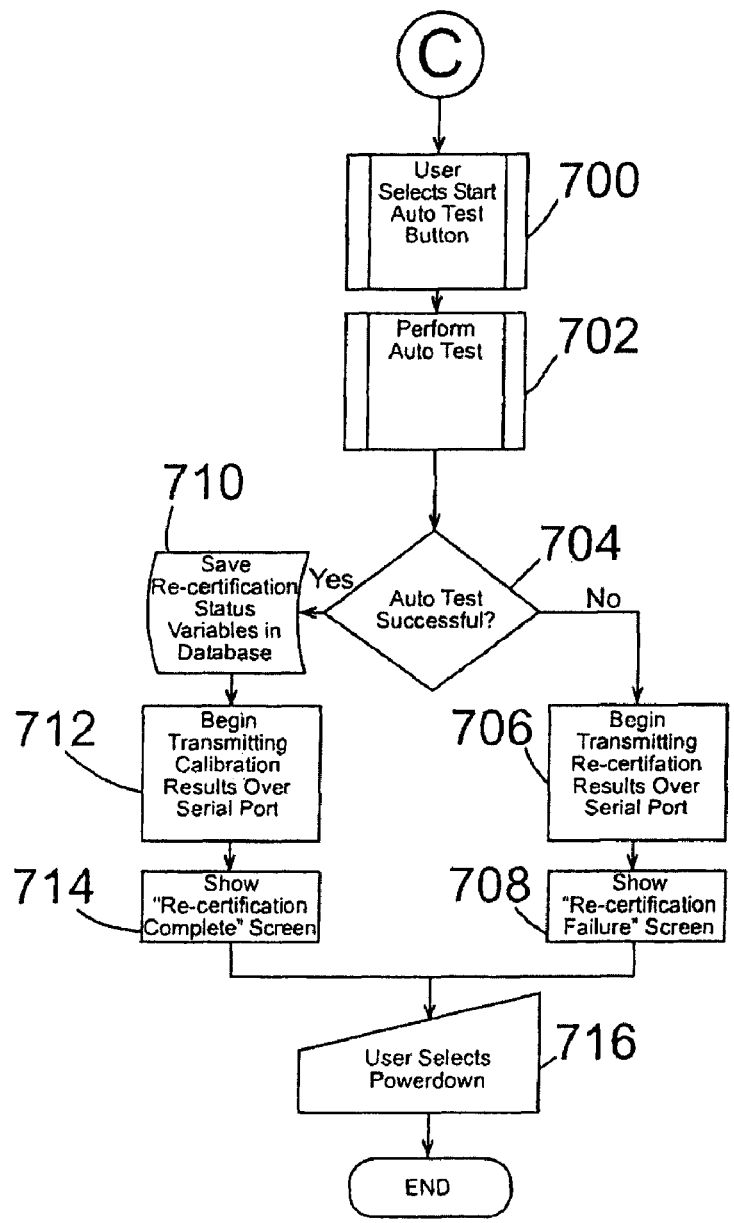
FIG. 4A is another sub-routine of the flow chart shown in FIG. 4 according to the present invention.
Figure 4B:
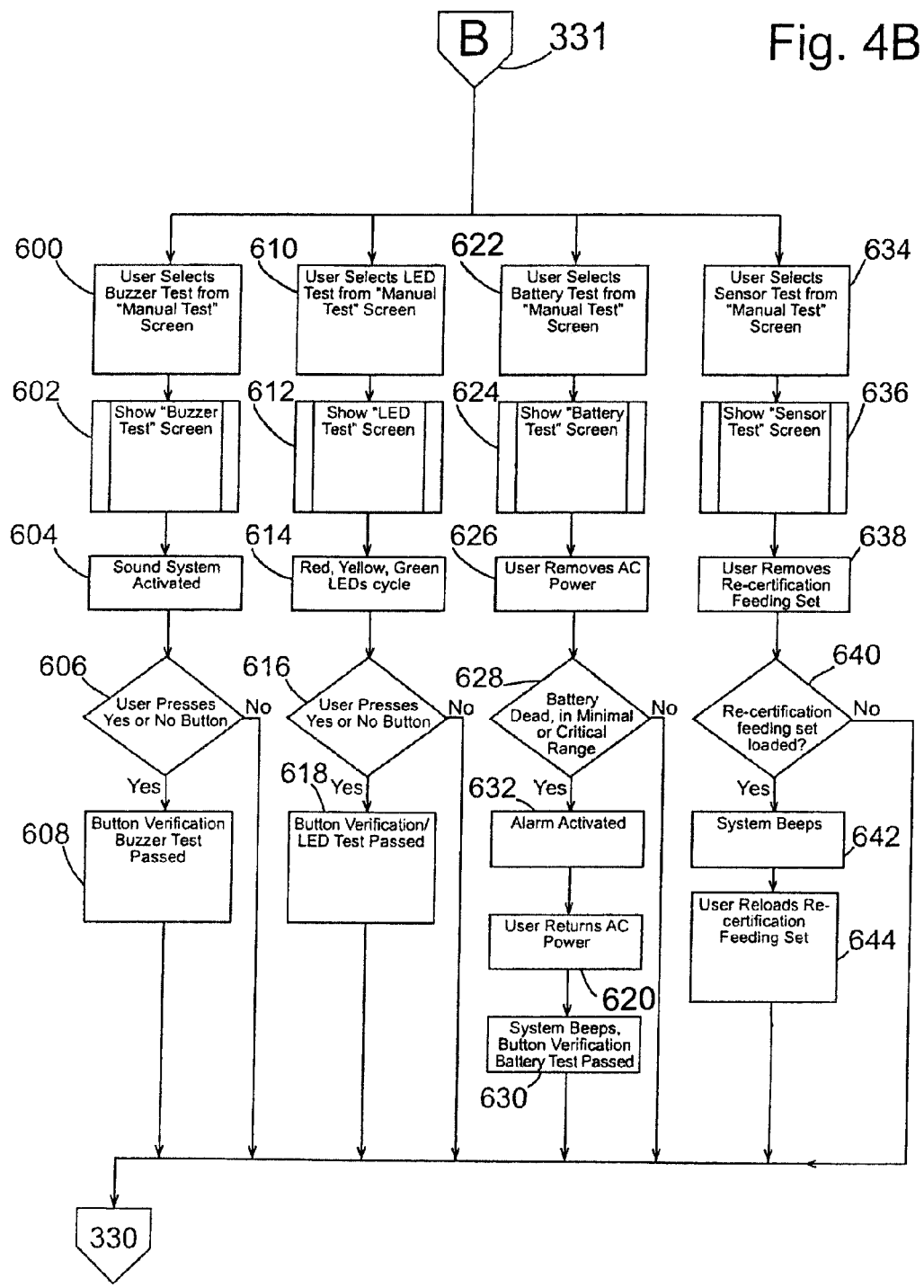
FIG. 4B is a sub-routine of the flow chart shown in FIG. 4 according to the present invention.

Referring to the flow charts in FIGS. 4, 4A and 4B, the various decision points and steps executed by software subsystem 36 under the re-certification procedure are illustrated. Software subsystem 36 directs flow control apparatus 10 to initiate a re-certification procedure when the re-certification feeding set 14 is loaded to the flow control apparatus 10.

At step 302, the software subsystem 36 reads database 134 to determine whether prior automatic and manual tests have been recently performed on the flow control apparatus 10 to determine whether components are functioning within a predetermined operational range. After this determination is made, software subsystem 36 at decision point 304 determines whether the re-certification feeding set 14 has been loaded to flow control apparatus 10 and sensed by sensor 30 when the mounting member 74 is engaged to second recess 60. If no re-certification feeding set 14 is sensed, then at step 306 the software subsystem again determines whether the manual and automatic tests have been performed.

At step 308, if neither the manual nor automatic tests have been performed, then the user interface 40 displays screen 400 (FIG. 5A) instructing the user to load the re-certification feeding set 14 to the flow control apparatus 10. At step 310, the user loads the re-certification feeding set 14 in the same manner described above for re-certification feeding set 14. If both the automatic and manual tests have been performed as determined at decision point 306, then at step 312 the software subsystem 36 instructs the flow control apparatus 10 to enter normal operation.

If at decision point 304, the re-certification feeding set 14 is determined to be loaded, then at decision point 316, the software subsystem 36 re-confirms whether the re-certification feeding set 14 is actually loaded to the flow control apparatus 10. If the re-certification feeding set 14 is not loaded, then at step 318 screen 400 (FIG. 5A) is shown again instructing the user to load the re-certification feeding set 14 to the flow control apparatus 10. At step 320, the user loads the re-certification feeding set 14 as instructed. Once step 320 is completed, screen 402 (FIG. 5B) is shown to the user at step 322 for displaying the main screen for performing the manual test according to the present invention.

At decision point 324, the software subsystem 36 determines whether the manual test has been performed. If not, then at step 326 button 510 for initiating the automatic test is hidden and disabled and software subsystem 36 proceeds to step 328. If the manual test has been performed, then at step 328, a re-iterative process subroutine B is executed at step 331 where the user is instructed to perform various manual tests for verifying that tested components of flow control apparatus 10 are functioning within a predetermined operational range by actuating buttons 500, 502, 506, and 508 at screen 402. These manual tests verify that the battery, LED light display, sound system, and sensor are functioning within a predetermined operational range as shall be discussed in greater detail below.

Referring to FIG. 4B the various decision points and steps executed by the software subsystem 36 when performing the various manual tests under subroutine B as well as the various screens and buttons presented to the user at user interface 40 for accomplishing the same are illustrated. At step 600, the user selects button 500 at screen 402 (FIG. 5B) which displays a buzzer test screen 404 (FIG. 5C) at step 602 which provides a means for verifying that the buzzer (not shown) or other sound system of flow control apparatus 10 is functioning within a predetermined operational range. The buzzer is then activated for the user to hear at step 604. At decision point 606, the user is queried whether the buzzer was heard and the user then presses either button 514 to signify YES or button 516 to signify NO or NOT SURE. At step 608, when the user presses button 514 software subsystem 36 verifies that button 514 is functional and also confirms the re-certification of the buzzer. If button 516 is pressed, at step 330 software subsystem 36 determines whether all of the manual tests have been performed and passed at step 330. If the software subsystem 36 enters step 330 because other manual tests are yet to be performed a reiterative process 331 is entered for performing the other manual tests under subroutine B.

At step 610, if the user selects button 502 at screen 402 then an LED Test screen 406 (FIG. 5D) is displayed at step 612 which provides a means for verifying that the LED lights 86 on user interface 40 are functioning within a predetermined operational range. The microprocessor 62 has LED lights 86 cycle through the red, yellow and green LED lights 86 at step 614. At decision point 616 the user is queried whether the LED lights 86 are actually cycling and the user presses either button 520 to signify YES or button 522 signifying NO. If the user presses button 520 then at step 618 the software subsystem 36 verifies that button 520 is operable and also re-certifies that LED lights 86 are functioning within a predetermined operational range. However, if the user presses button 522 then the software subsystem 36 at step 330 enters re-iterative process 331 for performing the other manual tests under subroutine B.

At step 622, if the user selects button 506 at screen 402 a screen 408 (FIG. 5E) is displayed at step 624 which provides step-by-step instructions to the user for performing a battery test on the battery (not shown) that provides power to the flow control apparatus 10. These step-by-step instructions instruct the user to disconnect AC power to the flow control apparatus 10 which will cause the LED lights 86 to dim. At decision point 626 the software subsystem 36 determines whether the battery is dead, or in a minimal or critical charge based upon predetermined values stored in database 134. If the battery is dead, or in a minimal or critical charge the software subsystem 36 at step 632 activates an alarm. After the alarm has been activated, the user is then instructed to reconnect the AC power to the flow control apparatus 10 at step 628. However, if the battery is not dead, or in a minimal or critical charge then software subsystem 36 enters re-iterative process 331 for performing the other manual tests at step 328.

At step 634, if the user selects button 508 at screen 402 then a screen 410 (FIG. 5F) is displayed at step 636 which provides instructions to the user for performing a manual test which verifies that sensor 30 can sense the loading of the re-certification feeding set 14 to the second recess 60, and in particular sensing the engagement of the mounting member 74 to second recess 60. Screen 410 instructs the user to remove the re-certification feeding set 14 from the flow control apparatus 10 at step 638. Once the sensor 30 senses the removal of re-certification feeding set 14 from the flow control apparatus 10, the buzzer is sounded at step 640 by the software subsystem 36. At step 642, the user reloads the re-certification feeding set 14A to the flow control apparatus 10 as described above. Once the re-certification feeding set 14A is loaded, the software subsystem 36 activates the buzzer, verifies that the sensor 30 can sense the engagement of the mounting member 74 to the second recess 60, and confirms that button 508 is operational. A button 530 is provided at screen 410 to cancel this procedure if so desired by the user.

Once it is confirmed that all of the manual tests have been performed at decision point 330, software subsystem 36 at step 332 displays and enables button 510 at screen 402 for allowing the user to start the automatic test during execution of a subroutine C at step 334.

At step 334 the automatic test is performed under subroutine C. The user first presses button 510 at screen 402 to begin the automatic test which provides a re-certification procedure that verifies that at least one component of the flow control apparatus 10 related to driving fluid through the re-certification feeding set 14, such as the rotor 26, gear arrangement 34 and single motor source 44, are functioning within a predetermined operational range. A screen 412 (FIG. 5G) is shown to the user that displays an "IN PROGRESS" message to the user signifying that the automatic test is being performed by software subsystem 36 at step 702. Once the automatic test is initiated, the software subsystem 36 determines at decision point 704 whether the automatic test has been successful.

Figure 5A:
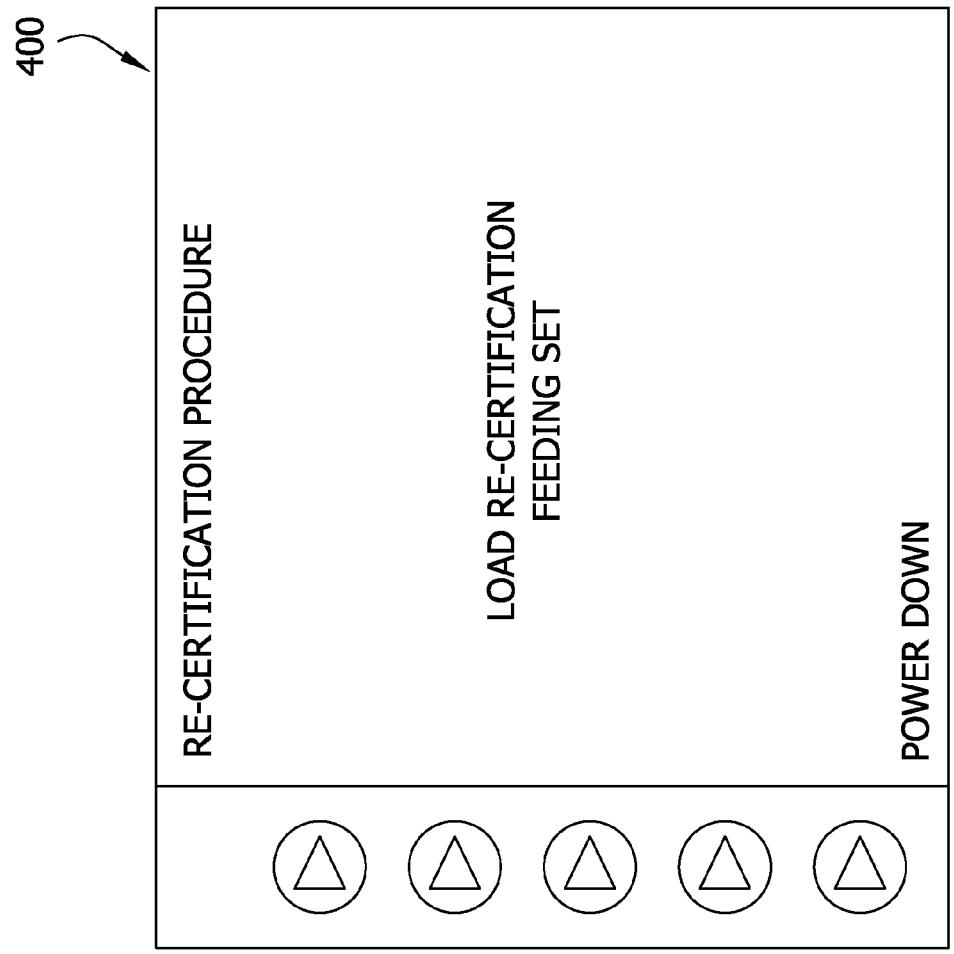
FIGS. 5A-I illustrate the sequence of screens shown to the user by the flow control apparatus to operate the recertification procedure according to the present invention.
Figure 5B:
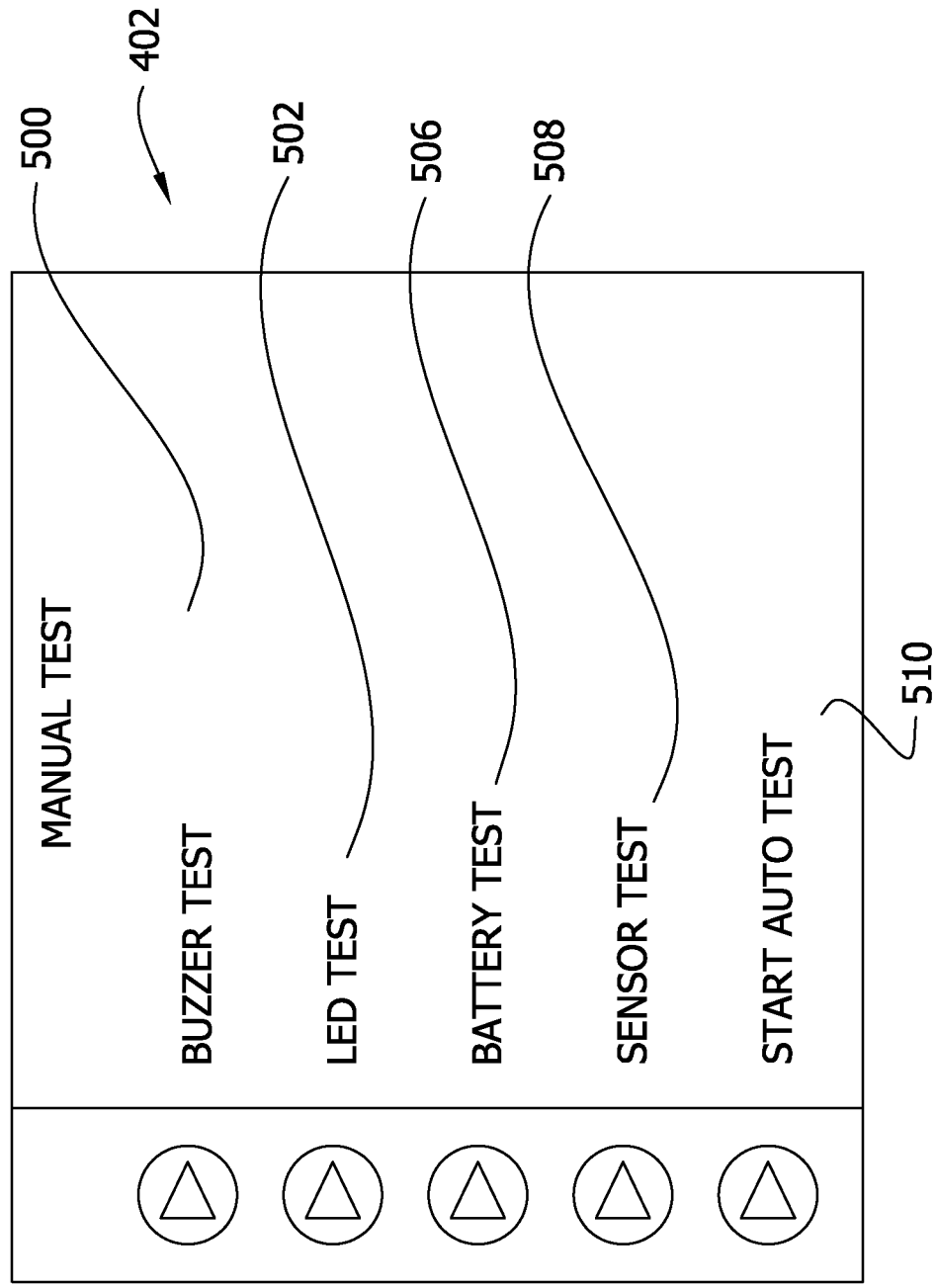
Figure 5C:
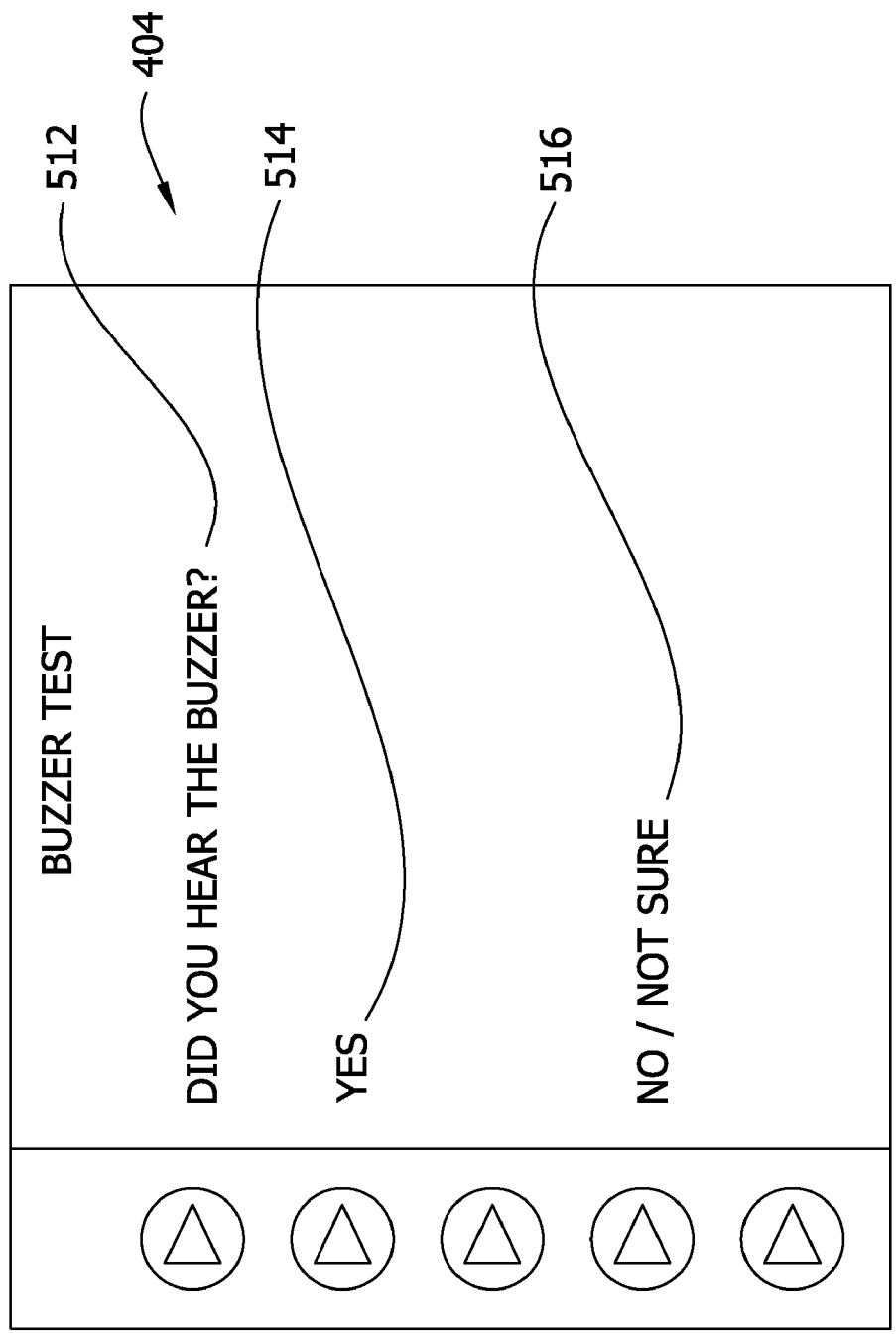
Figure 5D:
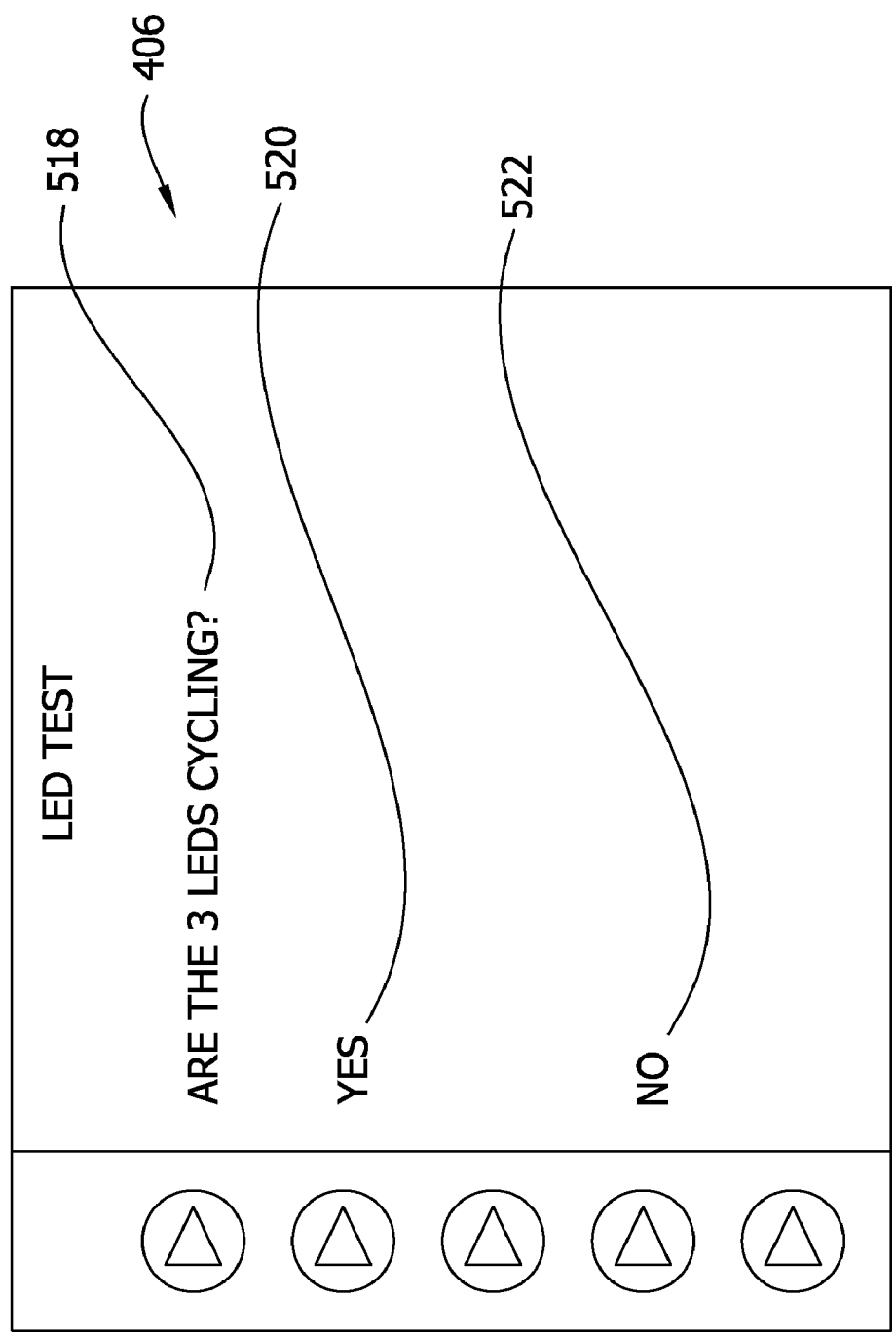
Figure 5E:
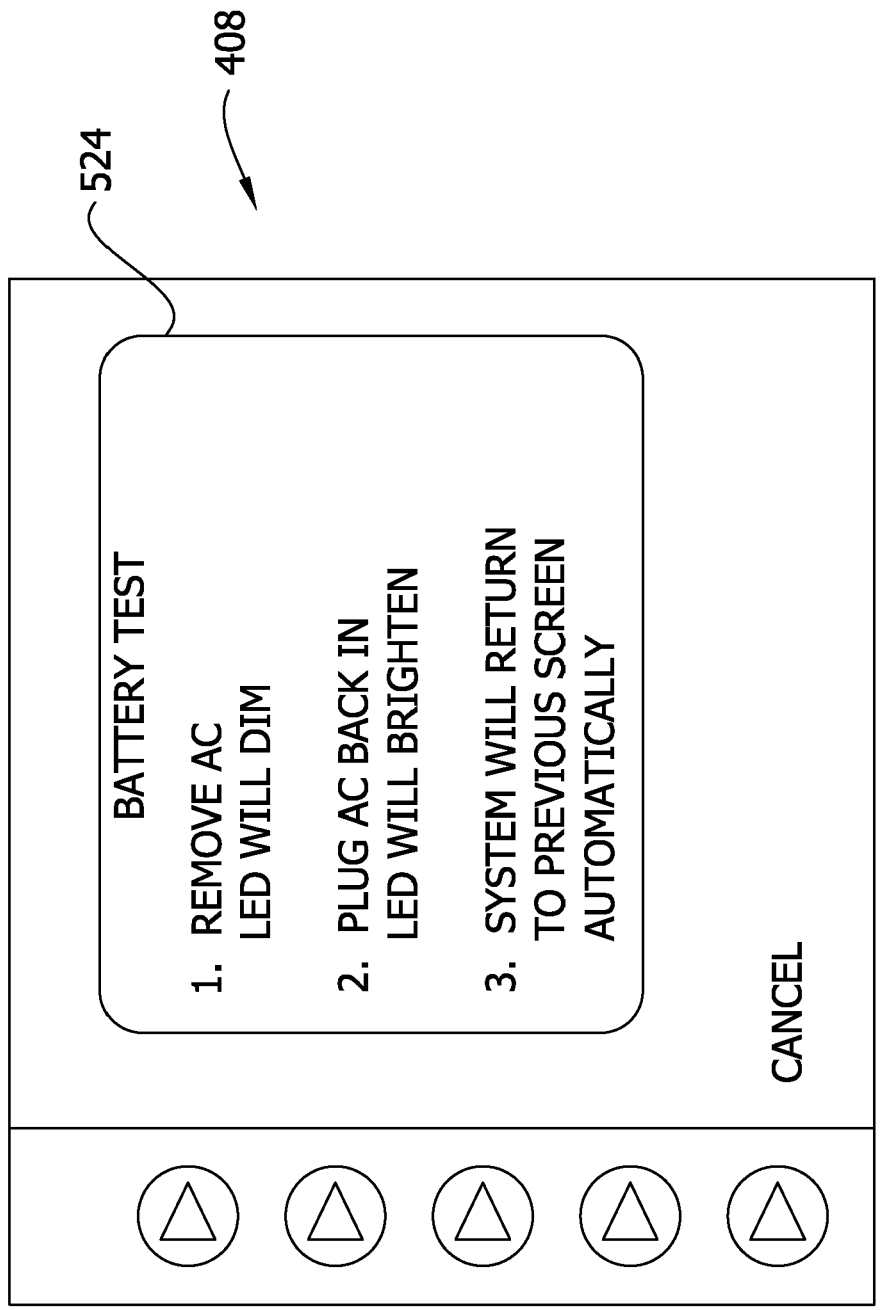
Figure 5F:
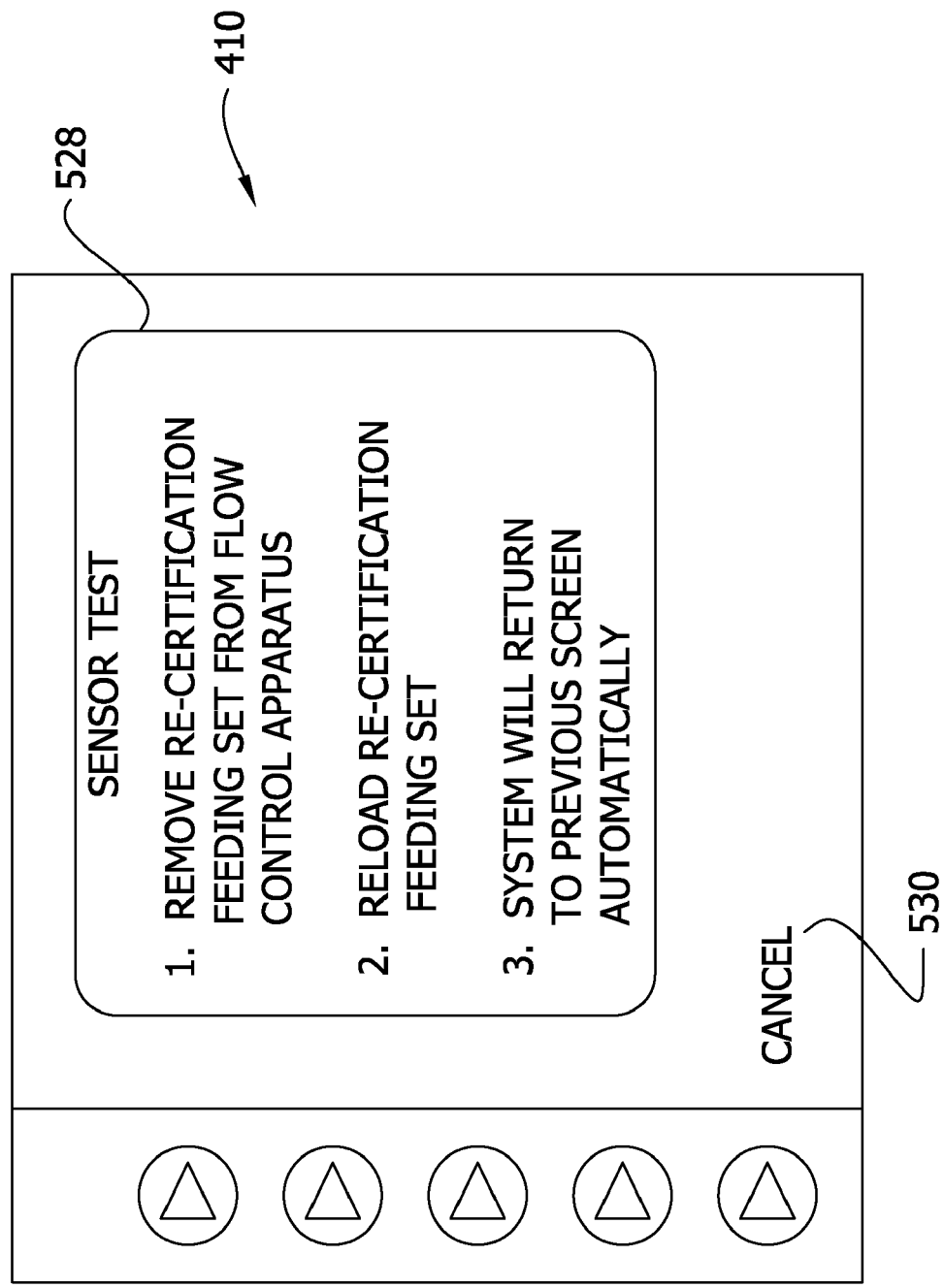
Figure 5G:
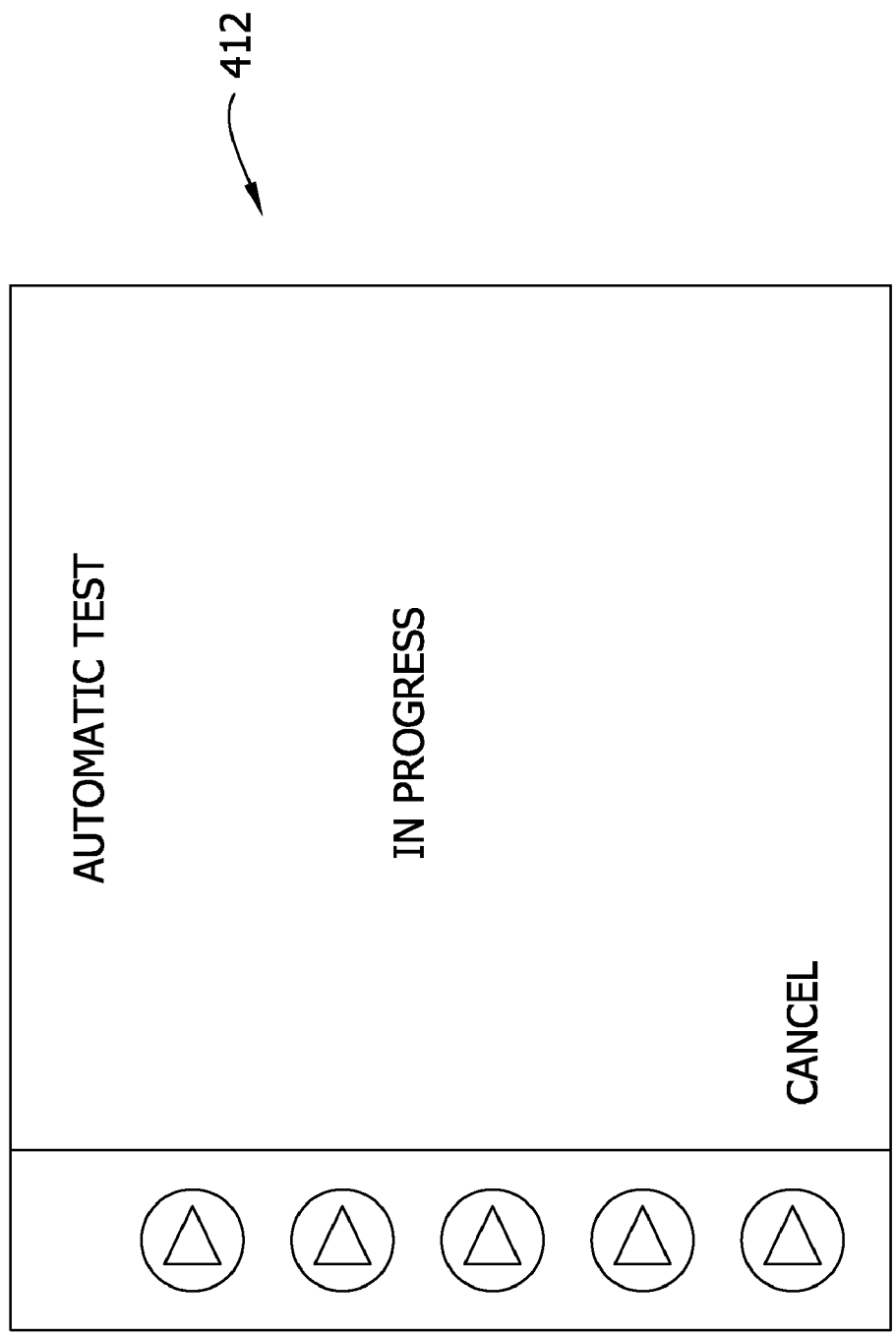
Figure 5H:
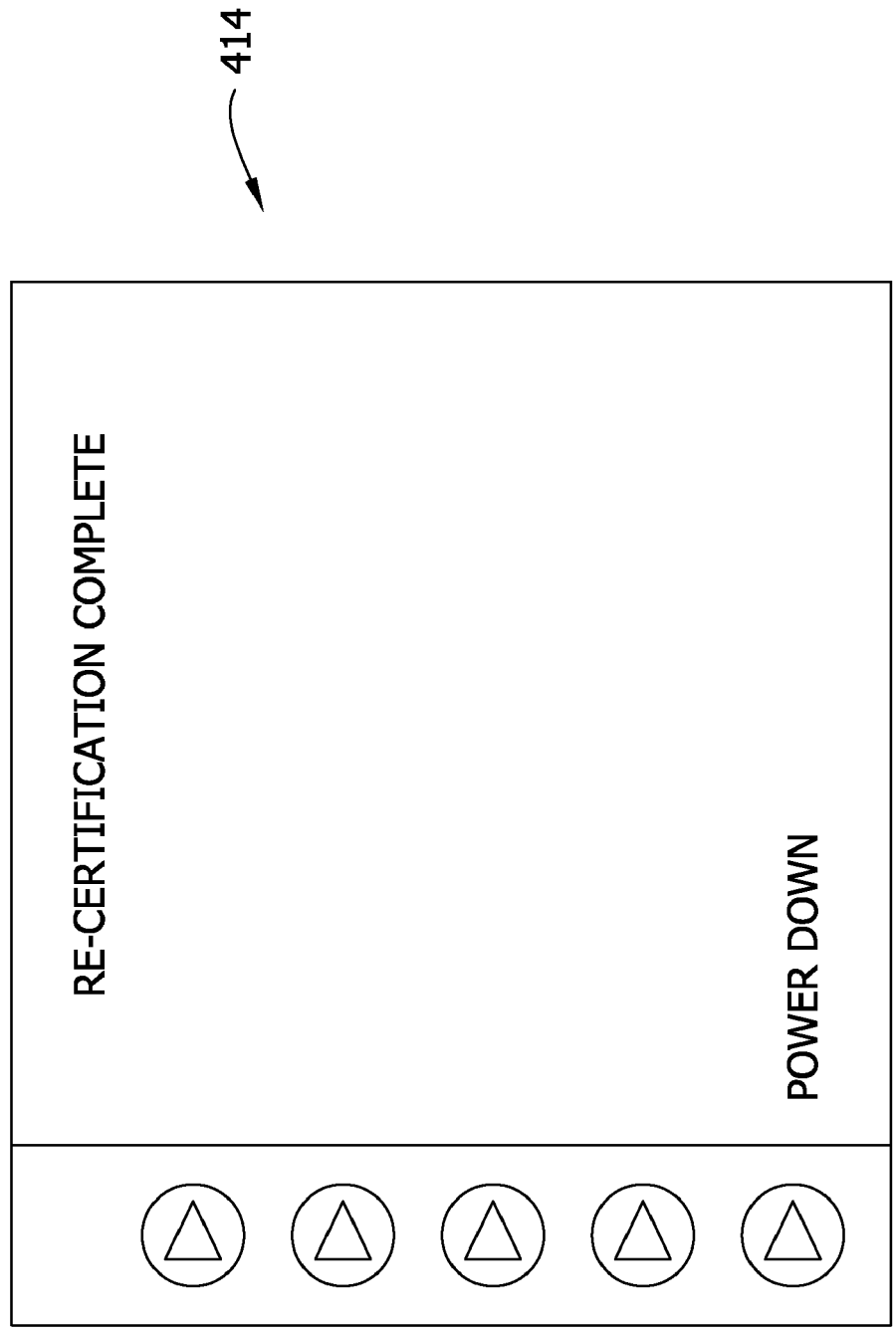
Figure 5I:
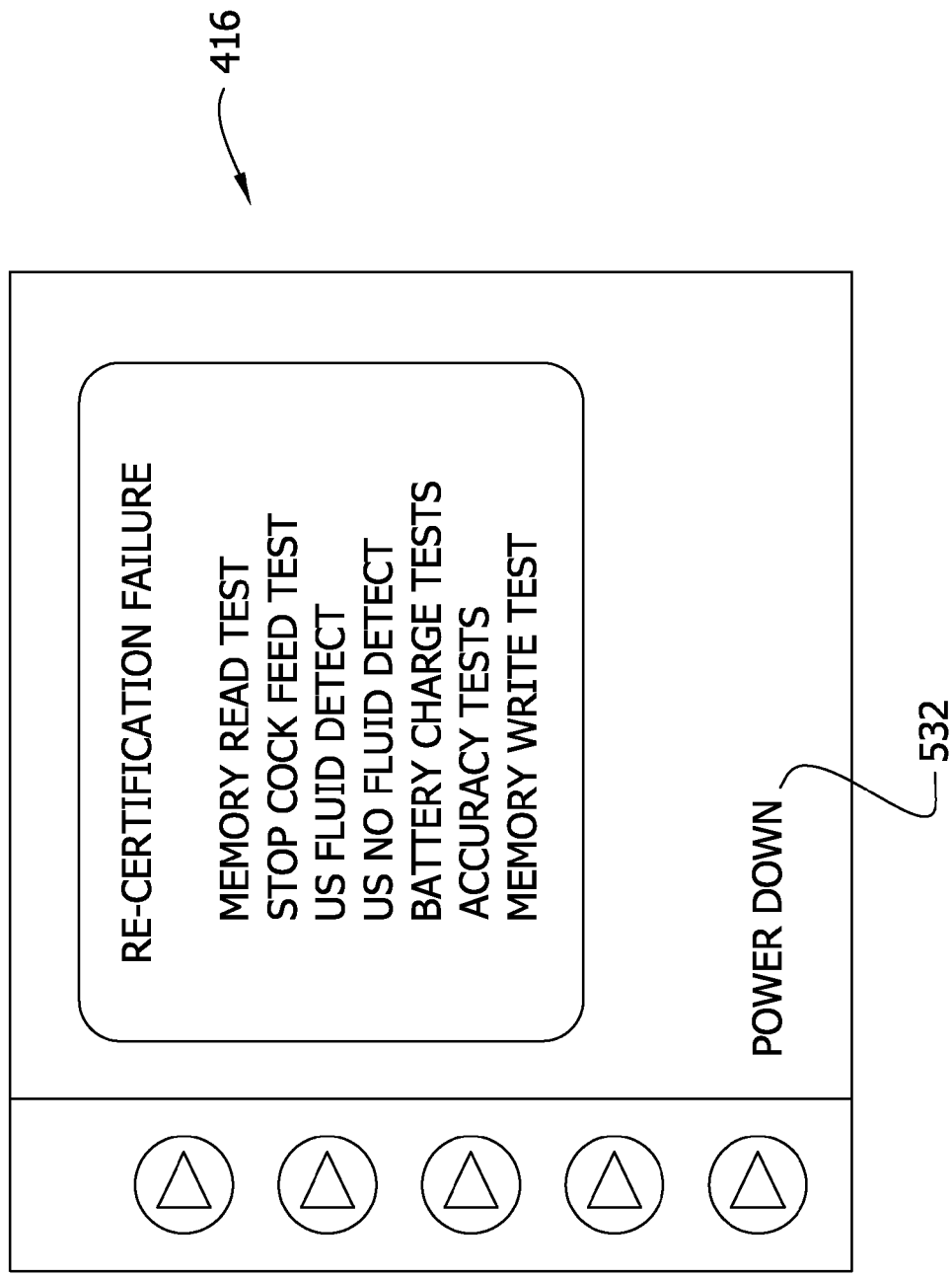

If the automatic test is not successful, then at step 706, the software subsystem 36 transmits test data over a serial port (not shown) of the flow control apparatus 10 to an external computer (not shown). At step 708, the software subsystem 36 displays a "RE-CERTIFICATION FAILURE" message to the user at screen 416 (FIG. 5I). After the message is displayed, at step 716 the user presses button 532 in order to power down the flow control apparatus 10 to complete subroutine C.

If the automatic test is successful, then at step 710, the software subsystem 36 saves the automatic test results to database 134. Once the automatic test results are saved, at step 712 the software subsystem 36 transmits test data over the serial port of the flow control apparatus 10 to the external computer.

After completion, a screen 414 (FIG. 5H) is shown to the user that displays a "RE-CERTIFICATION COMPLETE" message to the user at step 714. The software subsystem 36 at step 716 then instructs the user to power down the flow control apparatus 10 which completes the procedure of the re-certification system 12 according to the present invention.

It should be understood from the foregoing that, while particular embodiments of the invention have been illustrated and described, various modifications can be made thereto without departing from the spirit and scope of the invention as will be apparent to those skilled in the art.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions without departing from the scope of the invention, it is intended that all matter contained in the above description and shown in the accompanying drawings shall be interpreted as illustrative and not in a limiting sense.

What is claimed is:
1. A flow control apparatus comprising:
a flow control apparatus adapted to load a re-certification feeding set; and
a software subsystem in communication with the flow control apparatus comprising a re-certification procedure that determines whether a user has performed manual tests on the apparatus to verify that at least one component of the apparatus is functioning within a predetermined operational range, the subsystem disabling automatic testing if it determines that manual testing has not been performed and executing a reiterative process prompting the user to conduct manual testing if the subsystem determines that manual testing has been performed.

2. A flow control apparatus as set forth in claim 1 wherein the software subsystem prompts the user to conduct manual testing after the automatic testing is disabled.

3. A flow control apparatus as set forth in claim 2 wherein the manual tests verify that a battery of the flow control apparatus is functioning within a predetermined operational range.

4. A flow control apparatus as set forth in claim 2 wherein the manual tests verify that an LED light display of the flow control apparatus is functioning within a predetermined operational range.

5. A flow control apparatus as set forth in claim 2 wherein the manual tests verify that a sound system of the flow control apparatus is functioning within a predetermined operational range.

6. A flow control apparatus as set forth in claim 2 wherein the manual tests verify that a sensor of the flow control apparatus is functioning within a predetermined operational range.

7. A flow control apparatus as set forth in claim 2 wherein the software subsystem enables automatic testing after a confirmation that the manual tests have been performed, the subsystem prompting the user to conduct the automatic tests to verify that at least one component of the apparatus related to driving fluid through the re-certification feeding set is functioning within a predetermined operational range.

8. A flow control apparatus as set forth in claim 7 wherein the automatic tests verify that a rotor of the flow control apparatus is functioning within a predetermined operational range.

9. A flow control apparatus as set forth in claim 7 wherein the automatic tests verify that a gear arrangement of the flow control apparatus is functioning within a predetermined operational range.

10. A flow control apparatus as set forth in claim 7 wherein the automatic tests verify that a motor source of the flow control apparatus is functioning within a predetermined operational range.

11. A flow control apparatus as set forth in claim 7 wherein if the subsystem determines that the automatic tests were successful the subsystem saves the results to a database, displays a re-certification complete message, and prompts the user to power down the apparatus, and if the subsystem determines that the automatic tests were unsuccessful the subsystem displays a re-certification failure message and prompts the user to power down the apparatus.

12. A flow control apparatus comprising:
a flow control apparatus adapted to load a re-certification feeding set;
a sensor for sensing the loading of the re-certification feeding set to the flow control apparatus; and
a software subsystem in operative association with the sensor, wherein the software subsystem comprises a re-certification procedure to verify that at least one hardware component of the flow control apparatus related to driving fluid through the re-certification feeding set is functioning within a predetermined operational range.

13. A flow control apparatus as set forth in claim 12 wherein the at least one hardware component is one of a rotor, gear arrangement and motor of the apparatus.

* * * * *

Disclaimer

7,998,109—Robert B. Gaines, Lake Saint Louis, MO (US); Christopher A. Knauper, Lake St. Louis, MO (US); Jeffrey E. Price, Wildwood, MO (US). RE-CERTIFICATION SYSTEM FOR A FLOW CONTROL APPARATUS. Patent dated August 16, 2011. Disclaimer filed April 4, 2011, by the assignee, Covidien AG.

The term of this patent shall not extend beyond the expiration date of Pat. No. 7,794,432.
*(Official Gazette September 20, 2011)*